(12) United States Patent
Peterson et al.

(10) Patent No.: US 9,486,777 B2
(45) Date of Patent: Nov. 8, 2016

(54) PROCESS FOR PRODUCING WATER-ABSORBING POLYMER PARTICLES

(71) Applicant: BASF SE, Ludwigshafen (DE)

(72) Inventors: Monte Peterson, Pearland, TX (US); John Perry Guentzel, Beach City, TX (US); Gregory Boykin, Saraland, AL (US); Leo Van Miert, Kapellen (BE); Rene Callot, Ekeren (BE); Oskar Stephan, Hockenheim (DE); Rüdiger Funk, Niedernhausen (DE); Matthias Weismantel, Jossgrund-Oberndorf (DE)

(73) Assignee: BASF SE, Ludwigshafen (DE)

( * ) Notice: Subject to any disclaimer, the term of this patent is extended or adjusted under 35 U.S.C. 154(b) by 286 days.

(21) Appl. No.: 14/011,384

(22) Filed: Aug. 27, 2013

(65) Prior Publication Data

US 2014/0066584 A1 Mar. 6, 2014

Related U.S. Application Data

(60) Provisional application No. 61/694,284, filed on Aug. 29, 2012.

(51) Int. Cl.
| | |
|---|---|
| *B01J 20/26* | (2006.01) |
| *A61L 15/24* | (2006.01) |
| *A61L 15/60* | (2006.01) |
| *C08F 2/10* | (2006.01) |
| *C08F 6/00* | (2006.01) |
| *C08J 3/24* | (2006.01) |

(52) U.S. Cl.
CPC ............. *B01J 20/261* (2013.01); *A61L 15/60* (2013.01); *C08F 2/10* (2013.01); *C08F 6/008* (2013.01); *C08J 3/245* (2013.01); *B01J 2220/68* (2013.01); *C08J 2333/02* (2013.01)

(58) Field of Classification Search
CPC ... A61L 15/60; B01J 2220/68; B01J 20/261; C08J 2333/02
See application file for complete search history.

(56) References Cited

U.S. PATENT DOCUMENTS

| | | | |
|---|---|---|---|
| 6,291,636 B1 | 9/2001 | Miyake et al. | |
| 6,641,064 B1 * | 11/2003 | Dentler et al. | 241/24.28 |
| 7,682,702 B2 * | 3/2010 | Nitschke | 428/503 |
| 2009/0318633 A1 * | 12/2009 | Funk et al. | 525/451 |
| 2011/0166300 A1 * | 7/2011 | Dairoku et al. | 525/384 |
| 2012/0157644 A1 | 6/2012 | Fujino et al. | |

FOREIGN PATENT DOCUMENTS

| | | | |
|---|---|---|---|
| DE | 10 2005 055 077 A1 | 5/2007 | |
| EP | 0 497 623 A2 | 8/1992 | |
| EP | 497623 A2 * | 8/1992 | B29B 9/06 |
| EP | 0 508 810 A2 | 10/1992 | |
| EP | 0 574 248 A2 | 12/1993 | |
| EP | 0 948 997 A2 | 10/1999 | |
| JP | H06107800 A | 4/1994 | |
| JP | H0873518 A | 3/1996 | |

OTHER PUBLICATIONS

Designers, Specifiers and Buyers Handbook for Perforated Plate; IPA; 1993.*
Industrial Perforators Association. *Designers, Specifiers and Buyers Handbook for Perforated Metals* (1993), pp. 1-62, 63-124.
Third-Party Observation dated Dec. 19, 2014, filed in International Application No. PCT/EP2013/067609.
Buchholz, Fredric L., et al. *Modern Superabsorbent Polymer Technology*, "Commercial Processes for the Manufacture of Superabsorbent Polymers." New York: John Wiley & Sons, Inc., 1998, pp. 71-103.
International Search Report in international patent application No. PCT/EP2013/067609, dated Nov. 4, 2013.

* cited by examiner

*Primary Examiner* — Karuna P Reddy
(74) *Attorney, Agent, or Firm* — Marshall, Gerstein & Borun LLP

(57) ABSTRACT

The invention relates to a process for producing water-absorbing polymer particles, comprising polymerization, drying the resulting polymer gel on a through circulation belt dryer, crushing the dried polymer gel, pre-grinding, separating of incompletely dried particles with a perforated plate, grinding and classifying the resulting polymer particles.

14 Claims, 1 Drawing Sheet

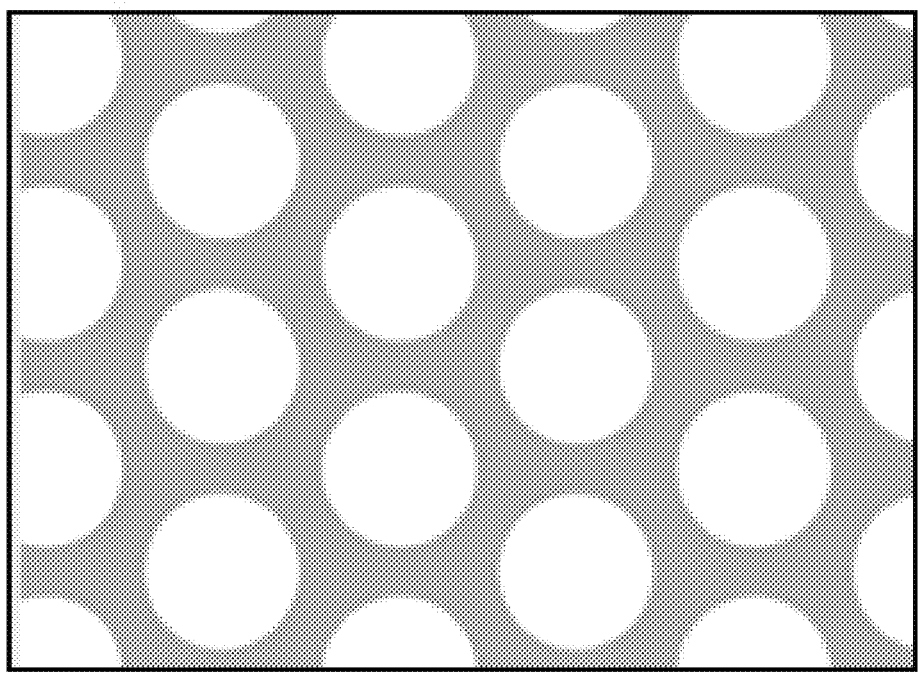

PROCESS FOR PRODUCING WATER-ABSORBING POLYMER PARTICLES

CROSS-REFERENCE TO RELATED APPLICATIONS

This application claims the benefit of U.S. provisional patent application No. 61/694,284, filed Aug. 29, 2012, incorporated herein by reference in its entirety.

The invention relates to a process for producing water-absorbing polymer particles, comprising polymerization, drying the resulting polymer gel on a through circulation belt dryer, crushing the dried polymer gel, pre-grinding, separating of incompletely dried particles with a perforated plate, grinding and classifying the resulting polymer particles.

Water-absorbing polymer particles are used to produce diapers, tampons, sanitary napkins and other hygiene articles, but also as water-retaining agents in market gardening. The water-absorbing polymer particles are often also referred to as "absorbent resins", "superabsorbents", "superabsorbent polymers", "absorbent polymers", "absorbent gelling materials", "hydrophilic polymers" or "hydrogels".

The production of water-absorbing polymer particles is described in the monograph "Modern Superabsorbent Polymer Technology", F. L. Buchholz and A. T. Graham, Wiley-VCH, 1998, pages 71 to 103.

The as-polymerized hydrogels are preferably dried on through circulation belt dryers. In the process, inhomogeneity mean that the gel layer is often dried non-uniformly in that either parts of the hydrogel have to be over-dried, causing product quality to suffer, or parts of the hydrogel are only incompletely dried. Incompletely dried polymeric particles lead to problems in subsequent processing steps and have to be separated off.

Processes for avoiding incompletely dried polymeric particles in drying are known for example from JP H06-73518, JP H06-107800, EP 0 497 623 A2, EP 0 508 810 A2 and EP 0 574 248 A2.

JP-H06-73518 describes a process for drying hydrogels on a belt dryer wherein dryer power output is continuously adjusted to current thickness of the gel layer whereby the fraction of incompletely dried polymeric particles is reduced.

JP-H06-107800 teaches that the over-drying and the separation of incompletely dried polymeric particles can be avoided by removing oversize lumps before drying.

EP 0 497 623 A2 discloses a process wherein the hydrogel is extruded before drying.

EP 0 508 810 A2 and EP 0 574 248 A2 teach the use of a specific kneader as a polymerization reactor whereby comparatively large hydrogel particles are avoided before drying.

The separation of incompletely dried polymeric particles is described in EP 0 948 997 A2, U.S. Pat. No. 6,641,064 and U.S. Pat. No. 7,682,702 for example.

EP 0 948 997 A2 and U.S. Pat. No. 6,641,064 disclose a process for continuous production of water-absorbing polymers wherein incompletely dried polymeric particles are separated off and if appropriate recycled into the drying stage.

U.S. Pat. No. 7,782,702 teaches the comminution of the separated incompletely dried polymeric particles prior to recycling into the drying stage.

The present invention has for its object to provide an improved process for continuous separation of incompletely dried polymeric particles.

The present invention has for its object to provide an improved process for continuous production of water-absorbing polymeric particles with reduced maintenance routine work.

The object was achieved by a process for producing water-absorbing polymer particles, comprising polymerization of a monomer solution or suspension, comprising a) at least one ethylenically unsaturated monomer which bears acid groups and may be at least partly neutralized, b) at least one crosslinker, c) at least one initiator, d) optionally one or more ethylenically unsaturated monomers copolymerizable with the monomers mentioned under a) and e) optionally one or more water-soluble polymers, drying the resulting polymer gel on a through circulation belt dryer, crushing the dried polymer gel, pre-grinding, separating of incompletely dried particles with a vibrating screen, grinding and classifying the resulting polymer particles, wherein the vibrating screen is a perforated plate having a thickness from 0.5 to 5 mm, an opening area from 20 to 80% and a hole diameter from 5 to 20 mm.

The thickness of the perforated plate is preferably from 0.75 to 4 mm, more preferably from 0.9 to 3 mm, most preferably from 1 to 2 mm. The perforated plate is preferably made of stainless steel. The opening area of the perforated plate is preferably from 30 to 70%, more preferably from 40 to 65%, most preferably from 45 to 60%. The opening area of the perforated plate is the sum of the area of all openings of the perforated plate divided by the area of the perforated plate. The diameter of the holes is preferably from 6.5 to 18 mm, more preferably from 8 to 16 mm, most preferably from 9 to 15 mm. The holes may have any shape as so long as the shortest and the longest opening distance is within the specified range. The holes are preferably of circular shape and the centers of the holes form equilateral triangles as shown in FIG. 1.

The present invention is based on the finding that the service life of the vibrating screen can be significantly improved by using perforated plates instead of using conventional screens.

The moisture content of the hydrogel after drying on a through circulation belt dryer is preferably less 10% by weight, more preferably less than 7.5% by weight, most preferably less than 5% by weight, the specified moisture contents merely being average values owing to possible inhomogeneity.

The moisture content of the separated incompletely dried polymeric particles is preferably at least 10% by weight, more preferably at least 15% by weight, most preferably at least 20% by weight.

The amount of the separated incompletely dried polymeric particles is preferably less than 50% by weight, more preferably less than 35% by weight, most preferably less than 25% by weight, based on the dried polymer gel.

The separated incompletely dried polymeric particles have higher moisture contents than the dried polymer gel. Customarily, the moisture content of the separated incompletely dried polymeric particles is in the range from 10% to 30% by weight, the moisture content customarily increasing with the particle diameter.

The dried polymer gel at the end of the through circulation belt dryer may have the shape of a porous sheet that must be crushed up by any suitable means. Preferably a toothed roll is used as crusher that may be part of the through circulation belt dryer.

The coarse polymer particles formed by crushing must be pre-grinded. Incompletely dried polymeric particles are elastic and merely deformed but not broken during pre-grinding. Coarse polymer particles having moisture content of less than 10% by weight are brittle and are pre-grinded to a median particle size of preferably from 0.1 to 15 mm, more preferably from 0.2 to 10 mm, most preferably from 0.3 to 8 mm. Any suitable means that fulfills these requirements can be used for pre-grinding. Preferably a roll mill is used or pre-grinding. The roll mill has a gap width of preferably from 1 to 10 mm, more preferably from 1.2 to 8 mm, most preferably from 1.5 to 6 mm.

After separation of the separated incomplete dried polymeric particles, the remaining dried polymeric particles are grinded. Useful means for grinding are pin mills, hammer mills or vibratory mills. Preferably a multistage roll mill is used or grinding, preference being given to a stepwise reduction in gap width in product flow direction. Particular preference is given to three-stage roll mills. With increasing number of stages, the particle size distribution becomes narrower. A multistage roll mill in the context of this invention is, for example, a roll mill with a plurality of successive roll pairs or a plurality of successive roll mills with one roll pair each. The roll mills have a gap width of preferably from 0.1 to 1 mm, more preferably from 0.2 to 0.9 mm, most preferably from 0.25 to 0.8 mm.

In a preferred embodiment of the present invention, the separated incomplete dried polymeric particles are further dried. Useful dryers for drying the separated incomplete dried polymeric particles are not subject to any restriction. Preferably a contact dryer such as, for example, a paddle dryer or a disk dryer, is used for such drying.

In a more preferred embodiment of the present invention, the separated incomplete dried polymeric particles are cut prior to further drying. Preferably a cutting mill is used for such cutting.

In a most preferred embodiment of the present invention, the separated incomplete dried polymeric particles are separated with a set of two vibrating screens having perforated plates. The hole diameter of the upper perforated plate is preferably at least 0.5 mm, more preferably at least 1 mm, most preferably at least 2 mm, larger than the hole diameter of the lower perforated plate. It is very particularly preferred to cut only the incompletely dried particles that are separated by the upper perforated plate prior to further drying.

Cutting the incompletely dried particles, especially of the larger ones, improves further drying of such particles.

The production of the water-absorbing polymer particles is described in detail hereinafter:

The water-absorbing polymer particles are produced by polymerizing a monomer solution or suspension, and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301

A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight and most preferably 0.3 to 0.6% by weight, based in each case on monomer a). With rising crosslinker content, the centrifuge retention capacity (CRC) falls and the absorption under a pressure of 21.0 g/cm$^2$ passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. However, the reducing component used is preferably disodium 2-hydroxy-2-sulfonatoacetate or a mixture of disodium 2-hydroxy-2-sulfinatoacetate, disodium 2-hydroxy-2-sulfonatoacetate and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

For better control of the polymerization reaction, it is optionally possible to add all known chelating agents to the monomer solution or suspension or to the raw materials thereof. Suitable chelating agents are, for example, phosphoric acid, diphosphoric acid, triphosphoric acid, polyphosphoric acid, citric acid, tartaric acid, or salts thereof.

Further suitable examples are iminodiacetic acid, hydroxyethyliminodiacetic acid, nitrilotriacetic acid, nitrilotripropionic acid, ethylenediaminetetraacetic acid, diethylenetriaminepentaacetic acid, triethylenetetraaminehexaacetic acid, N,N-bis(2-hydroxyethyl)glycine and trans-1,2-diaminocyclohexanetetraacetic acid, and salts thereof. The amount used is typically 1 to 30 000 ppm based on the monomers a), preferably 10 to 1000 ppm, preferentially 20 to 600 ppm, more preferably 50 to 400 ppm, most preferably 100 to 300 ppm.

The monomer solution or suspension is polymerized. Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms a polymer gel which has to be comminuted in a further process step, for example in an extruder or kneader.

To improve the drying properties, the comminuted polymer gel obtained by means of a kneader can additionally be extruded.

The acid groups of the resulting polymer gels have typically been partially neutralized. Neutralization is preferably carried out at the monomer stage. This is typically accomplished by mixing in the neutralizing agent as an aqueous solution or preferably also as a solid. The degree of neutralization is preferably from 50 to 90 mol %, more preferably from 60 to 85 mol % and most preferably from 65 to 80 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably from 10 to 30 mol % and more preferably from 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The resulting polymer gel is dried on a through-circulation belt dryer until the residual moisture content is preferably 0.5 to 10% by weight, more preferably 1 to 7% by weight and most preferably 2 to 5% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent crushing and grinding steps, undesirably large amounts of polymer particles with an excessively low particle size are obtained ("fines"). The solids content of the gel before the drying is preferably from 25 to 90% by weight, more preferably from 35 to 70% by weight and most preferably from 40 to 60% by weight. The dried polymer gel is crushed for pre-sizing. The crusher may be part of the through-circulation belt dryer.

Subsequently, the dried polymer gel is crushed, pre-grinded, separated from incompletely dried particles, grinded and classified.

The mean particle size of the polymer particles removed as the product fraction is preferably at least 200 µm, more preferably from 250 to 600 µm and very particularly from 300 to 500 µm. The mean particle size of the product fraction may be determined by means of EDANA recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of at least 150 µm is preferably at least 90% by weight, more preferably at least 95% by weight, most preferably at least 98% by weight.

Polymer particles with too small a particle size lower the saline flow conductivity (SFC). The proportion of excessively small polymer particles ("fines") should therefore be low.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated for, for example, by adjusting the amount of crosslinker b) used.

When the excessively small polymer particles are added at a very late stage, for example not until an apparatus connected downstream of the polymerization reactor, for example an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 µm is preferably at least 90% by weight, more preferably at least 95% by weight, most preferably at least 98% by weight.

The proportion of particles having a particle size of at most 600 µm is preferably at least 90% by weight, more preferably at least 95% by weight, most preferably at least 98% by weight.

Polymer particles of excessively large particle size lower the free swell rate. The proportion of excessively large polymer particles should therefore likewise be small.

Excessively large polymer particles are therefore typically removed and recycled into the grinding of the dried polymer gel.

To improve the properties, the polymer particles may subsequently be thermally surface postcrosslinked. Suitable surface postcrosslinkers are compounds which comprise groups which can form covalent bonds with at least two acid groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and derivatives thereof in WO 2003/031482 A1.

Preferred surface postcrosslinkers are ethylene carbonate, ethylene glycol diglycidyl ether, reaction products of polyamides with epichlorohydrin and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably 0.001 to 2% by weight, more preferably 0.02 to 1% by weight and most preferably 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight and more preferably 0.02 to 0.8% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are dried thermally, and the surface postcrosslinking reaction can take place either before or during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lodige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting behavior and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The thermal surface postcrosslinking is preferably performed in contact driers, more preferably paddle driers, most preferably disk driers. Suitable driers are, for example, Hosokawa Bepex® Horizontal Paddle Dryer (Hosokawa Micron GmbH; Leingarten; Germany), Hosokawa Bepex® Disc Dryer (Hosokawa Micron GmbH; Leingarten; Germany) and Nara Paddle Dryer (NARA Machinery Europe; Frechen; Germany). Moreover, fluidized bed driers may also be used.

The thermal surface postcrosslinking can be effected in the mixer itself, by heating the jacket or blowing in warm air. Equally suitable is a downstream drier, for example a shelf drier, a rotary tube oven or a heatable screw. It is particularly advantageous to effect mixing and drying in a fluidized bed drier.

Preferred surface postcrosslinking temperatures are in the range of 100 to 250° C., preferably 120 to 220° C., more preferably 130 to 210° C. and most preferably 150 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is preferably performed at 30 to 80° C., more preferably at 35 to 70° C., most preferably at 40 to 60° C. At excessively low temperatures, the water-absorbing polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the free swell rate and the saline flow conductivity (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The water-absorbing polymer particles produced by the process according to the invention have a centrifuge retention capacity (CRC) of typically at least 15 g/g, preferably at least 20 g/g, more preferably at least 22 g/g, especially preferably at least 24 g/g and most preferably at least 26 g/g. The centrifuge retention capacity (CRC) of the water-absorbing polymer particles is typically less than 60 g/g. The centrifuge retention capacity (CRC) is determined by EDANA recommended test method No. WSP 241.2-05 "Fluid Retention Capacity in Saline, After Centrifugation".

The water-absorbing polymer particles produced by the process according to the invention have an absorption under a pressure of 49.2 g/cm$^2$ of typically at least 15 g/g, preferably at least 20 g/g, more preferably at least 22 g/g, especially preferably at least 24 g/g and most preferably at least 26 g/g. The absorption under a pressure of 49.2 g/cm$^2$ of the water-absorbing polymer particles is typically less than 35 g/g. The absorption under a pressure of 49.2 g/cm$^2$ is determined analogously to EDANA recommended test method No. WSP 242.2-05 "Absorption under Pressure, Gravimetric Determination", except that a pressure of 49.2 g/cm$^2$ is established instead of a pressure of 21.0 g/cm$^2$.

Methods

The measurements should, unless stated otherwise, be carried out at an ambient temperature of 23±2° C. and a relative air humidity of 50±10%. The water-absorbing polymer particles are mixed thoroughly before the measurement.

Centrifuge Retention Capacity

The centrifuge retention capacity (CRC) of the water-absorbing polymer particles is determined by EDANA recommended test method No. WSP 241.2-05 "Centrifuge Retention Capacity".

The EDANA test methods are obtainable, for example, from EDANA, Avenue Eugene Plasky 157, B-1030 Brussels, Belgium.

EXAMPLES

Example 1

By continuously mixing deionized water, 50% by weight sodium hydroxide solution and acrylic acid, an acrylic acid/sodium acrylate solution was prepared, such that the degree of neutralization corresponds to 71.3 mol %. The solids content of the monomer solution was 38.8% by weight.

The polyethylenically unsaturated crosslinker used was polyethylene glycol-400 diacrylate (diacrylate proceeding from a polyethylene glycol with a mean molar mass of 400 g/mol). The amount used was 2 kg of crosslinker per t of monomer solution.

To initiate the free-radical polymerization, 1.03 kg of a 0.25% by weight aqueous hydrogen peroxide solution, 3.10 kg of a 15% by weight aqueous sodium peroxodisulfate solution and 1.05 kg of a 1% by weight aqueous ascorbic acid solution were used per t of monomer solution.

The throughput of the monomer solution was 20 t/h. The reaction solution had a temperature of 23.5° C. at the feed.

The individual components were metered in the following amounts continuously into a List Contikneter continuous kneader reactor with a capacity of 6.3 m³ (LIST AG, Arisdorf, Switzerland):

| | |
|---|---|
| 20 t/h | of monomer solution |
| 40 kg/h | of polyethylene glycol-400 diacrylate |
| 82.6 kg/h | of hydrogen peroxide solution/sodium peroxodisulfate solution |
| 21 kg/h | of ascorbic acid solution |

Between the addition point for the crosslinker and the addition sites for the initiators, the monomer solution was inertized with nitrogen.

After approx. 50% of the residence time, a metered addition of fines (1000 kg/h), which were obtained from the production process by grinding and screening, to the reactor additionally took place. The residence time of the reaction mixture in the reactor was 15 minutes.

The resulting polymer gel was placed onto a through circulation belt dryer. On the through circulation belt dryer, an air/gas mixture flowed continuously around the polymer gel and dried it. The residence time in the belt dryer was 37 minutes. The dried Polymer gel was crushed at the end of the through circulation belt dryer using a toothed roll.

The coarse polymer particles formed by crushing were pre-grinded with roll mill having a gap width of 1.5 mm. This was followed by separation of incompletely dried particles with a set of two vibrating screens having perforated plates. The upper perforated plate had a thickness of 1.3 mm, an opening area of 51% and a hole diameter 14.3 mm. The lower perforated plate had a thickness of 1.3 mm, an opening area of 51% and a hole diameter 9.5 mm. The holes have a circular shape and the centers of the holes form equilateral triangles. The service life of the perforated plates was more than one year.

The separated incompletely dried particles were dried in a disk dryer, pre-grinded and recycled to separation of the incompletely dried particles. Incompletely dried particles that were separated by the upper perforated plate were cut prior to further drying using a cutting mill.

The dried polymer gel was grinded using a three stage roll mill and screened off to a particle size fraction of 150 to 850 µm. The resulting base polymer was surface postcrosslinked.

In a Schugi Flexomix® (Hosokawa Micron B.V., Doetinchem, the Netherlands), the base polymer was coated with a surface postcrosslinker solution and then dried in a NARA paddle dryer (GMF Gouda, Waddinxveen, the Netherlands) at 190° C. for 45 minutes. The paddle dryer was heated with steam having a pressure of 24 bar (220° C.).

The following amounts were metered into the Schugi Flexomix®:

| | |
|---|---|
| 7.5 t/h | of base polymer |
| 270.0 kg/h | of surface postcrosslinker solution |

The surface postcrosslinker solution comprised 2.8% by weight of 2-hydroxyethyl-2 oxazolidone, 2.8% by weight of aluminum sulfate, 66.1% by weight of deionized water and 28.3% by weight of isopropanol.

After being dried, the surface postcrosslinked base polymer was cooled to approx. 60° C. in a NARA paddle cooler (GMF Gouda, Waddinxveen, the Netherlands).

The resulting water-absorbing polymer particles had a centrifuge retention capacity (CRC) of 28.4 g/g.

Example 2 (Comparative Example)

Example 1 was repeated, except that the set of perforated plates used for separation of incompletely dried particles was replaced by screens of comparable mesh size. The service life of the screens was approximately 4 month.

The invention claimed is:

1. A process for producing water-absorbing polymer particles, comprising polymerization of a monomer solution or suspension, comprising
   a) at least one ethylenically unsaturated monomer which bears an acid group and may be at least partly neutralized,
   b) at least one crosslinker,
   c) at least one initiator,
   d) optionally one or more ethylenically unsaturated monomer copolymerizable with the monomer mentioned under a), and
   e) optionally one or more water-soluble polymer,
   drying the resulting polymer gel on a through circulation belt dryer, crushing the dried polymer gel, pre-grinding the crushed and dried polymer gel to provide coarse polymer particles, separating incompletely dried particles from the coarse dried polymer particles with a set of two vibrating screens having perforated plates, grinding the coarse dried polymer particles, and classifying resulting coarse dried polymer particles, wherein the vibrating screen is a perforated plate having a thickness from 0.5 to 5 mm, an opening area from 20 to 80%, and a hole diameter from 5 to 20 mm.

2. The process according to claim 1, wherein a moisture content of the incompletely dried particles is at least 10% by weight.

3. The process according to claim 1, wherein the dried polymer gel is crushed by means of a toothed roll.

4. The process according to claim 1, wherein the crushed particles are pre-grinded by means of a roller mill having a gap width of at least 1 mm.

5. The process according to claim 1, wherein the resulting coarse dried polymer particles are grinded by a multistage roller mill having a gap width of from 0.1 to 1 mm.

6. The process according to claim 1, wherein the separated incompletely dried particles are further dried by means of a contact dryer.

7. The process according to claim 1, wherein the separated incompletely dried particles are cut prior to further drying.

8. The process according to claim 1, wherein a hole diameter of an upper perforated plate is at least 2 mm larger than a hole diameter of a lower perforated plate.

9. The process according to claim 1, wherein only the incompletely dried particles that are separated by the upper perforated plate are cut prior to further drying.

10. The process according to claim 1, wherein a proportion of acrylic acid in the total amount of ethylenically unsaturated monomer a) is at least 95 mol %.

11. The process according to claim 1, wherein a degree of neutralization of the ethylenically unsaturated monomer a) is from 65 to 80 mol %.

12. The process according to claim 1, wherein the amount of crosslinker b) based on monomer a) is 0.3 to 0.6% by weight.

13. The process according to claim 1, wherein the water-absorbing polymer particles have a centrifuge retention capacity of at least 15 g/g.

14. The process according to claim 1, wherein the water-absorbing polymer particles are further surface postcrosslinked.

* * * * *